(12) United States Patent
Maxson et al.

(10) Patent No.: US 9,700,414 B2
(45) Date of Patent: Jul. 11, 2017

(54) METHOD AND APPARATUS FOR PRE-FORMING A HIGH TIBIAL OSTEOTOMY

(71) Applicant: Biomet Sports Medicine, LLC, Warsaw, IN (US)

(72) Inventors: William Maxson, Fort Wayne, IN (US); Gautam Gupta, Warsaw, IN (US)

(73) Assignee: Biomet sports Medicine, LLC, Warsaw, IN (US)

( * ) Notice: Subject to any disclaimer, the term of this patent is extended or adjusted under 35 U.S.C. 154(b) by 0 days.

(21) Appl. No.: 14/579,583

(22) Filed: Dec. 22, 2014

(65) Prior Publication Data
US 2015/0148904 A1    May 28, 2015

Related U.S. Application Data

(62) Division of application No. 13/720,644, filed on Dec. 19, 2012, now Pat. No. 8,920,512.

(51) Int. Cl.
*A61B 17/80* (2006.01)
*A61F 2/28* (2006.01)
*A61F 2/30* (2006.01)

(52) U.S. Cl.
CPC ........ *A61F 2/2846* (2013.01); *A61B 17/8095* (2013.01); *A61F 2/28* (2013.01); *A61F 2002/2892* (2013.01); *A61F 2002/30112* (2013.01); *A61F 2002/30266* (2013.01); *A61F 2002/30538* (2013.01);
(Continued)

(58) Field of Classification Search
CPC ............ A61B 17/8095; A61B 17/0401; A61B 2017/564; A61F 2/28; A61F 2002/30736; A61F 2002/30011; A61F 2002/3631; A61F 2002/30131; A61F 2002/30281; A61F 2002/30538; A61F 2250/0024
See application file for complete search history.

(56) References Cited

U.S. PATENT DOCUMENTS 4,421,112 A    12/1983    Mains et al.
5,053,039 A    10/1991    Hofmann et al.
(Continued)

FOREIGN PATENT DOCUMENTS

FR             2741525 A1    5/1997
FR             2771282 A1    5/1999
WO    WO-2014099619 A1    6/2014

OTHER PUBLICATIONS

"Arthrex® iBalance® HTO System for Medial Hight Tibial Opening Wedge Osteotomy—Surgical Technique," Medical brochure. (2013) 16 sheets.
(Continued)

*Primary Examiner* — Ann Schillinger
(74) *Attorney, Agent, or Firm* — Schwegman Lundberg & Woessner, P.A.

(57) ABSTRACT

An osteotomy implant including a porous portion, a solid portion, and a hinge portion. The porous portion includes a first part and a second part that defines a clearance therebetween. A solid portion abuts the porous portion. A hinge portion of the solid portion is coupled to the first part and the second part. The hinge portion is configured to enable the implant to be changed from a first configuration to a second configuration.

14 Claims, 3 Drawing Sheets

(52) U.S. Cl.
CPC ............... *A61F 2002/30736* (2013.01); *A61F 2230/0013* (2013.01); *A61F 2250/0006* (2013.01)

(56) References Cited

U.S. PATENT DOCUMENTS

| | | | |
|---|---|---|---|
| 5,084,051 A * | 1/1992 | Tormala et al. | 606/77 |
| 5,364,402 A | 11/1994 | Mumme et al. | |
| 5,417,694 A | 5/1995 | Marik et al. | |
| 5,613,969 A | 3/1997 | Jenkins, Jr. | |
| 5,620,448 A | 4/1997 | Puddu | |
| 5,722,978 A | 3/1998 | Jenkins, Jr. | |
| 5,921,988 A | 7/1999 | Legrand | |
| 6,086,593 A | 7/2000 | Bonutti | |
| 6,514,259 B2 | 2/2003 | Picard et al. | |
| 6,823,871 B2 | 11/2004 | Schmieding | |
| 7,060,074 B2 | 6/2006 | Rosa et al. | |
| 7,104,997 B2 | 9/2006 | Lionberger et al. | |
| 7,121,832 B2 | 10/2006 | Hsieh et al. | |
| 7,935,119 B2 | 5/2011 | Ammann et al. | |
| 7,959,637 B2 | 6/2011 | Fox et al. | |
| 7,967,823 B2 | 6/2011 | Ammann et al. | |
| 8,062,301 B2 | 11/2011 | Ammann et al. | |
| 8,083,749 B2 | 12/2011 | Taber | |
| 8,133,230 B2 | 3/2012 | Stevens et al. | |
| 8,137,406 B2 | 3/2012 | Novak et al. | |
| 8,167,951 B2 | 5/2012 | Ammann et al. | |
| 8,182,489 B2 | 5/2012 | Horacek | |
| 8,192,441 B2 | 6/2012 | Collazo | |
| 8,192,495 B2 | 6/2012 | Simpson et al. | |
| 8,211,112 B2 * | 7/2012 | Novak | A61B 17/8095 606/87 |
| 8,241,292 B2 | 8/2012 | Collazo | |
| 8,241,293 B2 | 8/2012 | Stone et al. | |
| 8,265,790 B2 | 9/2012 | Amiot et al. | |
| 8,303,596 B2 | 11/2012 | Plaβky et al. | |
| 8,333,772 B2 | 12/2012 | Fox et al. | |
| 8,355,773 B2 | 1/2013 | Leitner et al. | |
| 8,632,547 B2 | 1/2014 | Maxson et al. | |
| 8,920,512 B2 | 12/2014 | Maxson et al. | |
| 2003/0105526 A1 | 6/2003 | Bryant et al. | |
| 2004/0153087 A1 | 8/2004 | Sanford et al. | |
| 2005/0033432 A1 * | 2/2005 | Gordon et al. | 623/17.11 |
| 2005/0075641 A1 * | 4/2005 | Singhatat et al. | 606/86 |
| 2005/0228393 A1 | 10/2005 | Williams et al. | |
| 2005/0234465 A1 | 10/2005 | McCombs et al. | |
| 2005/0240195 A1 | 10/2005 | Axelson et al. | |
| 2005/0273114 A1 | 12/2005 | Novak | |
| 2006/0195111 A1 | 8/2006 | Couture | |
| 2006/0200158 A1 | 9/2006 | Farling et al. | |
| 2006/0241635 A1 | 10/2006 | Stumpo et al. | |
| 2006/0241636 A1 | 10/2006 | Novak et al. | |
| 2006/0293681 A1 | 12/2006 | Claypool et al. | |
| 2007/0016209 A1 | 1/2007 | Ammann et al. | |
| 2007/0118138 A1 | 5/2007 | Seo et al. | |
| 2007/0244487 A1 | 10/2007 | Ammann et al. | |
| 2007/0288029 A1 | 12/2007 | Justin et al. | |
| 2007/0288030 A1 | 12/2007 | Metzger et al. | |
| 2008/0015603 A1 | 1/2008 | Collazo | |
| 2008/0015604 A1 | 1/2008 | Collazo | |
| 2008/0015605 A1 | 1/2008 | Collazo | |
| 2008/0039850 A1 | 2/2008 | Rowley et al. | |
| 2008/0097451 A1 | 4/2008 | Chen et al. | |
| 2008/0140081 A1 | 6/2008 | Heavener et al. | |
| 2008/0140213 A1 | 6/2008 | Ammann et al. | |
| 2008/0147073 A1 | 6/2008 | Ammann et al. | |
| 2008/0161816 A1 | 7/2008 | Stevens et al. | |
| 2008/0195109 A1 | 8/2008 | Hunter et al. | |
| 2008/0287954 A1 | 11/2008 | Kunz et al. | |
| 2008/0294170 A1 | 11/2008 | O'Brien | |
| 2008/0306485 A1 | 12/2008 | Coon et al. | |
| 2009/0076520 A1 | 3/2009 | Choi | |
| 2009/0082774 A1 | 3/2009 | Oti et al. | |
| 2009/0088759 A1 | 4/2009 | Aram et al. | |
| 2009/0088760 A1 | 4/2009 | Aram et al. | |
| 2009/0099567 A1 | 4/2009 | Zajac | |
| 2009/0118769 A1 | 5/2009 | Sixto, Jr. et al. | |
| 2009/0131942 A1 | 5/2009 | Aker et al. | |
| 2009/0222015 A1 | 9/2009 | Park et al. | |
| 2009/0248044 A1 | 10/2009 | Amiot et al. | |
| 2009/0287217 A1 | 11/2009 | Ammann et al. | |
| 2009/0318921 A1 | 12/2009 | White et al. | |
| 2010/0010493 A1 | 1/2010 | Dower | |
| 2010/0023015 A1 | 1/2010 | Park | |
| 2010/0042105 A1 | 2/2010 | Park et al. | |
| 2010/0049195 A1 | 2/2010 | Park et al. | |
| 2010/0057088 A1 | 3/2010 | Shah | |
| 2010/0121334 A1 | 5/2010 | Couture et al. | |
| 2010/0145344 A1 | 6/2010 | Jordan et al. | |
| 2010/0168752 A1 | 7/2010 | Edwards | |
| 2010/0191244 A1 | 7/2010 | White et al. | |
| 2010/0198224 A1 | 8/2010 | Metzger et al. | |
| 2010/0212138 A1 | 8/2010 | Carroll et al. | |
| 2010/0217338 A1 | 8/2010 | Carroll et al. | |
| 2010/0318088 A1 | 12/2010 | Warne et al. | |
| 2011/0015636 A1 | 1/2011 | Katrana et al. | |
| 2011/0015639 A1 | 1/2011 | Metzger et al. | |
| 2011/0022049 A1 | 1/2011 | Huebner et al. | |
| 2011/0166578 A1 | 7/2011 | Stone et al. | |
| 2011/0172672 A1 | 7/2011 | Dubeau et al. | |
| 2011/0184419 A1 | 7/2011 | Meridew et al. | |
| 2011/0218634 A1 * | 9/2011 | Ringeisen | A61B 17/80 623/17.18 |
| 2011/0251617 A1 | 10/2011 | Ammann et al. | |
| 2011/0269100 A1 | 11/2011 | Furrer et al. | |
| 2011/0275032 A1 | 11/2011 | Tardieu et al. | |
| 2012/0109138 A1 | 5/2012 | Meridew et al. | |
| 2012/0130382 A1 | 5/2012 | Iannotti et al. | |
| 2012/0141034 A1 | 6/2012 | Iannotti et al. | |
| 2012/0143197 A1 | 6/2012 | Lang et al. | |
| 2012/0143267 A1 | 6/2012 | Iannotti et al. | |
| 2012/0215225 A1 | 8/2012 | Philippon et al. | |
| 2012/0221017 A1 | 8/2012 | Bonutti | |
| 2012/0232596 A1 | 9/2012 | Ribeiro | |
| 2012/0259335 A1 | 10/2012 | Scifert et al. | |
| 2012/0271314 A1 | 10/2012 | Stemniski et al. | |
| 2012/0276509 A1 | 11/2012 | Iannotti et al. | |
| 2012/0283840 A1 | 11/2012 | Frederick et al. | |
| 2012/0289965 A1 | 11/2012 | Gelaude et al. | |
| 2012/0296339 A1 | 11/2012 | Iannotti et al. | |
| 2012/0303004 A1 | 11/2012 | Uthgenannt et al. | |
| 2012/0303033 A1 | 11/2012 | Weiner et al. | |
| 2012/0310399 A1 | 12/2012 | Metzger | |
| 2013/0006250 A1 | 1/2013 | Metzger et al. | |
| 2013/0035766 A1 | 2/2013 | Meridew | |
| 2013/0085500 A1 | 4/2013 | Meridew et al. | |
| 2013/0110116 A1 | 5/2013 | Kehres et al. | |
| 2013/0119579 A1 | 5/2013 | Iannotti et al. | |
| 2013/0131681 A1 | 5/2013 | Katrana et al. | |
| 2014/0172116 A1 | 6/2014 | Maxson et al. | |

OTHER PUBLICATIONS

"iBalance® HTO System Innovative Solutions for Varus Knee Realignment," Arthrex® medical brochure. (2013). 6 sheets.
"iBalance® Medial Opening Wedge Tibial System," Arthrex®. (2011). 63 sheets.
"Pro Osteon® 200 R Bone Graft Substitute," Biomet brochure. (2014) 1 sheet.
"Pro Osteon® 500R Bone Graft Substitute," Biomet brochure. (2014) 1 sheet.
"Regenerex® Porous Titanium Construct," Biomet brochure. (2008) 12 sheets.
International Search Report and Written Opinion mailed Mar. 13, 2014 for PCT/US2013/074723 claiming benefit of U.S. Appl. No. 13/720,644, filed Dec. 19, 2012.
"U.S. Appl. No. 13/720,644, Examiner Interview Summary mailed Jun. 12, 2014", 3 pgs.
"U.S. Appl. No. 13/720,644, Non Final Office Action mailed Mar. 6, 2014", 11 pgs.
"U.S. Appl. No. 13/720,644, Notice of Allowance mailed Aug. 19, 2014", 7 pgs.

(56) References Cited

OTHER PUBLICATIONS

"U.S. Appl. No. 13/720,644, Response filed Feb. 5, 2014 to Restriction Requirement mailed Dec. 5, 2013", 5 pgs.
"U.S. Appl. No. 13/720,644, Response filed Jun. 6, 2014 to Non Final Office Action mailed Mar. 6, 2014", 11 pgs.
"U.S. Appl. No. 13/720,644, Restriction Requirement mailed Dec. 5, 2013", 5 pgs.
"European Application Serial No. 13818070.8, Office Action mailed Jul. 28, 2015", 2 pgs.
"International Application Serial No. PCT/US2013/074723, International Preliminary Report on Patentability mailed Jul. 2, 2015", 8 pgs.
"European Application Serial No. 13818070.8, Communication Pursuant to Article 94(3) EPC mailed Jun. 27, 2016", 6 pgs.
"European Application Serial No. 13818070.8, Response filed Feb. 8, 2016 to Office Action mailed Jul. 28, 2015", 8 pgs.
"European Application Serial No. 13818070.8, Response filed Nov. 4, 2016 to Communication Pursuant to Article 94(3) EPC mailed Jun. 27, 2016", 14 pgs.

* cited by examiner

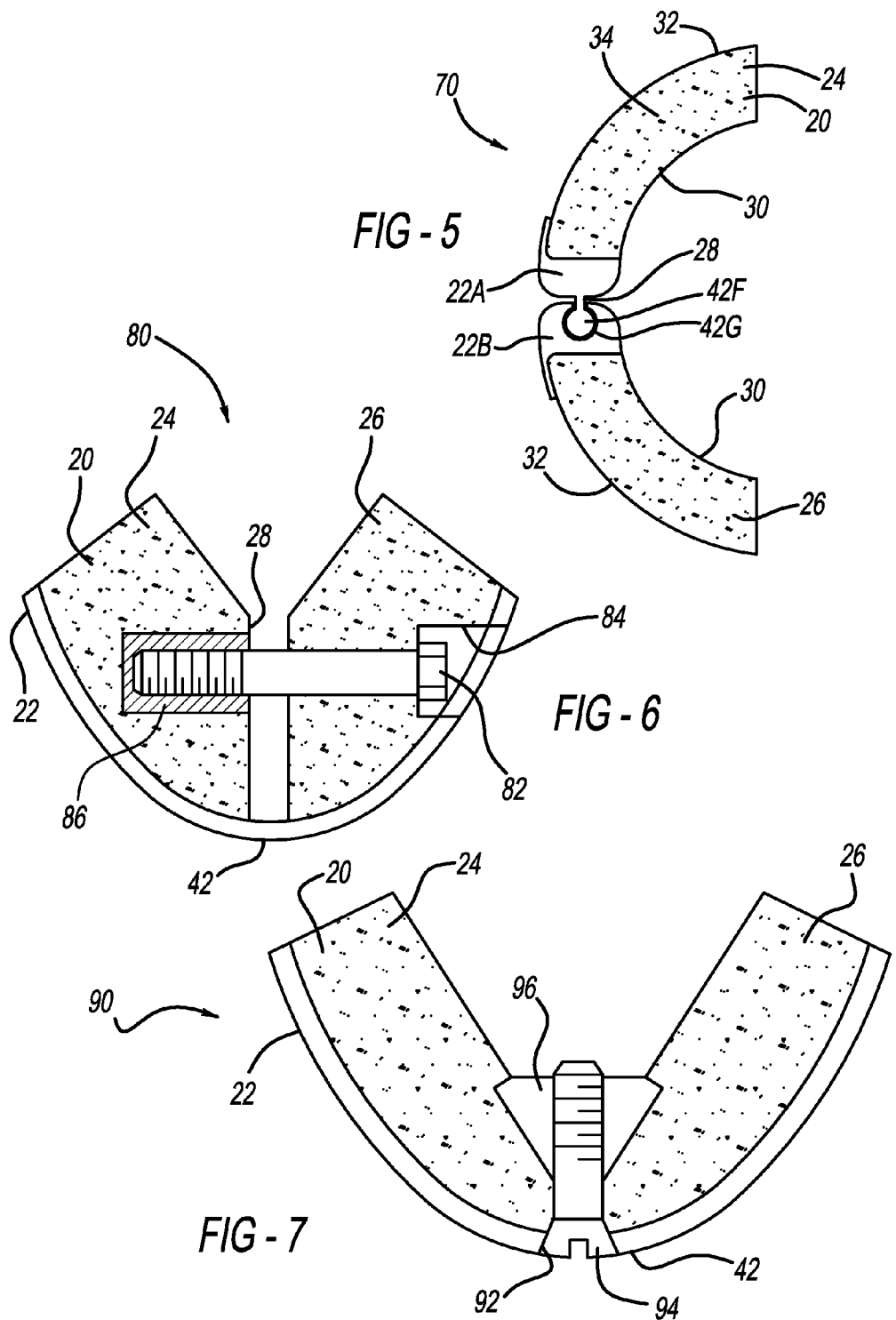

US 9,700,414 B2

METHOD AND APPARATUS FOR PRE-FORMING A HIGH TIBIAL OSTEOTOMY

CROSS-REFERENCE TO RELATED APPLICATIONS

This application is a divisional application of U.S. patent application Ser. No. 13/720,644 filed on Dec. 19, 2012, the entire disclosure of which is incorporated by reference herein.

FIELD

The present disclosure relates to a method and apparatus for pre-forming a high tibial osteotomy.

BACKGROUND

This section provides background information related to the present disclosure which is not necessarily prior art.

Various knee osteotomies are performed to adjust or change the orientation of the tibia to correct various abnormalities caused by birth defects, trauma, or disease. High tibial osteotomies include open-wedge and closed-wedge osteotomies. Various implants designed to fill osteotomies exist. Some are modeled after a patient's specific anatomy, which increases the cost of the implant and complexity of production. Therefore, a simplified and cost-effective osteotomy implant that can be adjusted to fit a patient's anatomy would be desirable.

SUMMARY

This section provides a general summary of the disclosure, and is not a comprehensive disclosure of its full scope or all of its features.

The present teachings provide for an osteotomy implant including a porous portion, a solid portion, and a hinge portion. The porous portion includes a first part and a second part that defines a clearance therebetween. A solid portion abuts the porous portion. A hinge portion of the solid portion is coupled to the first part and the second part. The hinge portion is configured to enable the implant to be changed from a first configuration to a second configuration.

The present teachings also provide for an osteotomy implant including a porous metallic portion, a solid metallic portion, and a metallic hinge portion. The porous metallic portion includes a first part spaced apart from a second part. The solid metallic portion is integral with the porous metallic portion. The metallic hinge portion of the solid metallic portion is one of aligned with or between the first part and the second part. The hinge portion is configured to enable the implant to be changed from a first configuration to a second configuration.

The present teachings also provide for an osteotomy implant including a generally "U" shaped loadbearing porous portion including a first part and a second part. The first part includes a first inner surface that opposes a second inner surface of the second part. A solid portion is coupled to both a first outer surface of the first part and a second outer surface of the second part. The first outer surface is opposite to the first inner surface and the second outer surface is opposite to the second inner surface. A flexible hinge portion is included with the solid portion. The implant is bendable at the flexible hinge portion to compress or expand the implant. The flexible hinge portion is configured to enable the implant to be changed from a first configuration to a second configuration.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 5 is a top view of yet another osteotomy implant according to the present teachings;

FIG. 6 is a top view of still another osteotomy implant according to the present teachings; and FIG. 7 is a top view of an additional osteotomy implant according to the present teachings.

Corresponding reference numerals indicate corresponding parts throughout the several views of the drawings.

DETAILED DESCRIPTION

Example embodiments will now be described more fully with reference to the accompanying drawings.

Figure 1:
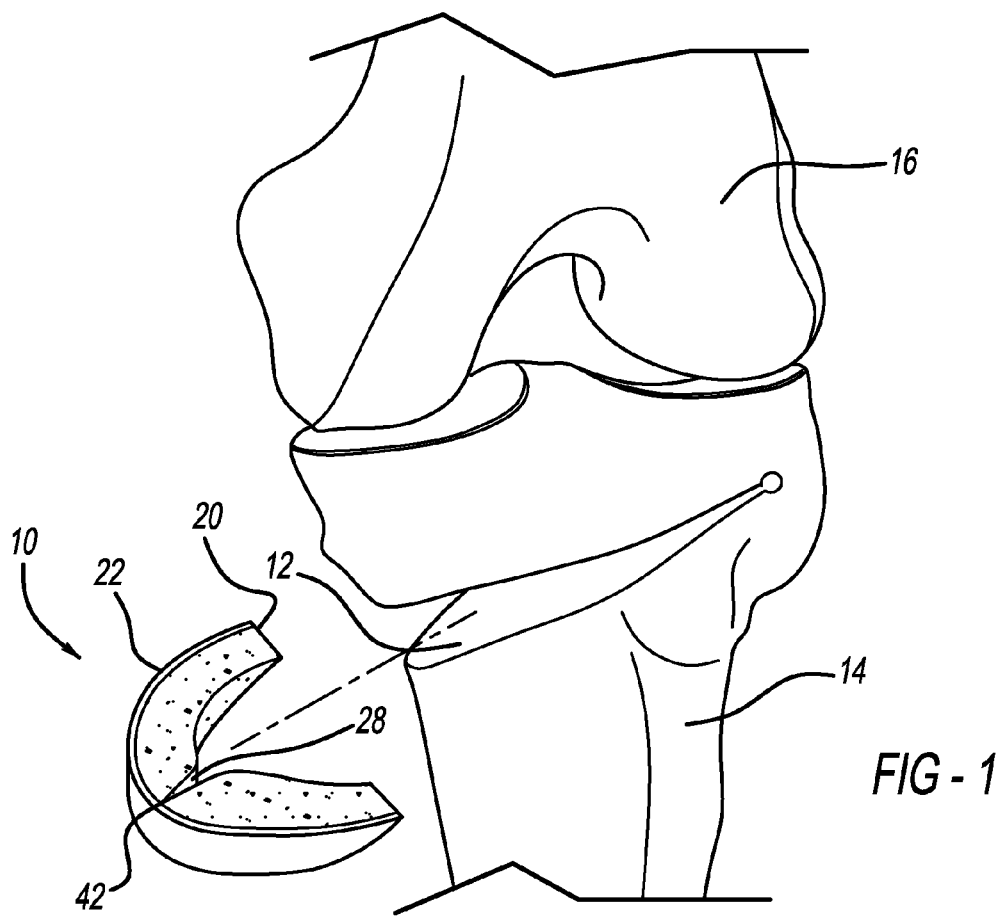
FIG. 1 illustrates an osteotomy implant according to the present teachings for implantation in an osteotomy site of a tibia bone.
Figure 2:
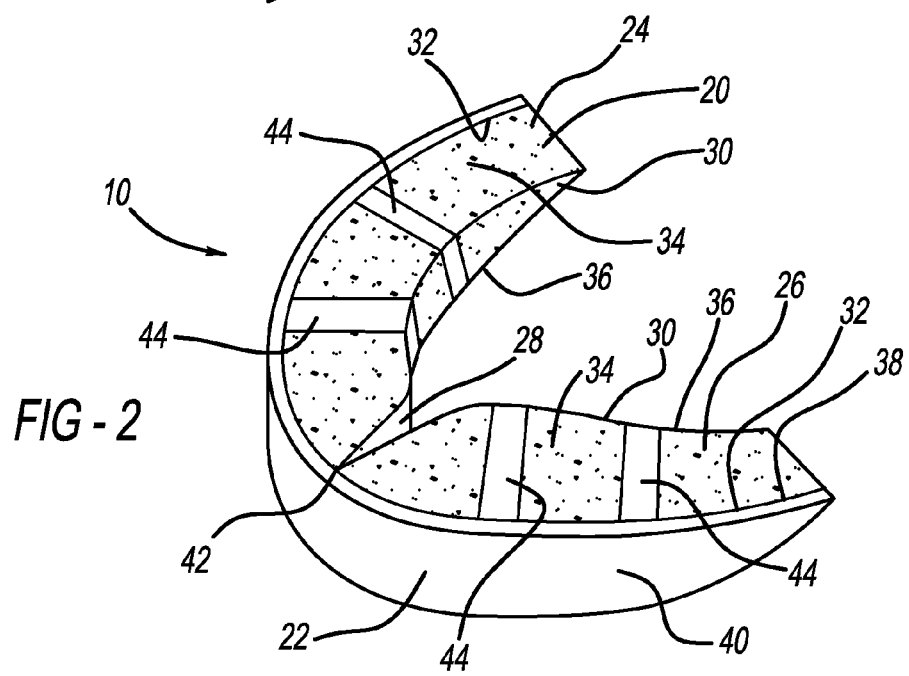
FIG. 2 is a perspective view of the implant of FIG. 1.

With initial reference to FIGS. 1 and 2, an osteotomy implant according to the present teachings is generally illustrated at reference numeral 10. As illustrated, the osteotomy implant 10 is for implantation at osteotomy site 12 of tibia 14. Femur 16 is also illustrated. The implant 10 can also be implanted at an osteotomy site in the femur 16, such as during a distal femoral osteotomy procedure.

The osteotomy implant 10 generally includes a porous portion 20 and a solid portion 22. The porous portion 20 generally includes a first part 24 and a second part 26, which define a clearance or gap 28 therebetween. Both the first part 24 and the second part 26 include an inner surface 30 and an outer surface 32, which is opposite to the inner surface 30. The first part 24 and the second part 26 are arranged such that the inner surface 30 of the first part 24 faces and is opposite to the inner surface 30 of the second part 26. Each of the first part 24 and the second part 26 further include an upper or superior surface 34, which is opposite to an under or inferior surface 36. The solid portion 22 includes an inner surface 38, which is opposite to an outer surface 40. The solid portion 22 extends across the outer surface 32 of each of the first part 24 and the second part 26 of the porous portion 20, and thus extends across the gap 28. The solid portion 22 includes a hinge 42, such as a living hinge, opposite to the gap 28.

The implant 10 can be made of any suitable biocompatible material sufficient to bear loads on the tibia 14 at the osteotomy site 12. For example, the implant 10 can be made out of a suitable metallic, such as titanium including commercially pure (CP) titanium or Grade 5 titanium alloy (Ti6Al4V). An example of a suitable porous titanium construct that the implant can be made from is Regenerex® by Biomet of Warsaw, Ind. Any suitable cobalt chrome based alloy may also be used. Both the porous portion 20 and the solid portion 22 can be made of the same material. The porous portion 20 can be made from any suitable implantable plastic, such as PEEK (polyether ether ketone) or PEKK (polyether ketone ketone). For example, the porous portion 20 can include ProOsteon® by Biomet of Warsaw, Ind.

The implant 10 can be manufactured in any suitable manner. For example, the porous portion 20 and the solid portion 22 can be individually manufactured and then subsequently coupled or joined together using any suitable coupling process. Other manufacturing processes that are suitable include electron beam melting or any suitable additive manufacturing process, such as a suitable additive metal fabrication technique. Using laser sintering, for example, the entire implant 10 can be manufactured or printed together, such that the porous portion 20 and the solid portion 22 are integrally formed and the implant 10 is monolithic. The porous portion 20 can be formed in any suitable manner that will provide for pores into which bone growth may occur in order to further secure the implant 10 at the osteotomy site 12. The porous portion 20 is a generally "U" shaped, load-bearing portion able to withstand loads upon the tibia 14. Upon being inserted into the osteotomy site 12, the implant 10 will be retained within the osteotomy site 12 through friction between the tibia 14 and the porous portion 20. The solid portion 22 further increases the compression strength of the implant 10 and prevents tissue from growing into the porous portion 20 from outside of the osteotomy site 12. The porous portion 22 may include ribs 44 to further increase the compression strength of the implant 10. The ribs 44 are structural, load-bearing ribs that are not porous.

Implantation of the implant 10 at the osteotomy site 12 will now be described. The implant 10 selected for implantation can be chosen from a plurality of implants 10 having a similar overall configuration, but having different general sizes to facilitate customization. For example, a plurality of implants 10 having different superior-inferior heights and medial-lateral widths can be provided and selected based on dimensions of the osteotomy size 12. The width of the implant 10 is first compared to the width of the osteotomy site 12 in the anterior to the posterior direction. The width of the implant 10 is generally considered with respect to the distance between the first part 24 and the second part 26 of the porous portion 20. If the width of the implant 10 is wider than the width of the osteotomy site 12, then the implant 10 can be compressed in order to decrease the width. If the width of the implant 10 is narrower than the width of the osteotomy site 12, then the implant 10 can be expanded in order to increase its width.

The implant 10 can be compressed (closed) or expanded (opened) either manually or using a suitable tool. The material of the solid portion 22 is rigid enough to maintain structural integrity of the implant 10, but flexible enough to permit the implant 10 to be compressed in this manner. As the first part 24 and the second part 26 are moved together, the gap 28 therebetween will become smaller. As the first part 24 and the second part 26 are moved apart, the gap 28 therebetween will become larger. Specifically, implant 10 pivots generally at the hinge 42, which can be configured in any suitable manner to facilitate bending of the solid portion 22, such as with a thinned portion, a notched portion, or any weakened portion. The first part 24 and the second part 26 can be compressed or expanded to any suitable position, such as between a first configuration and a second configuration, thus providing the implant 10 with a near infinite number of medial-lateral widths. The rigidity of the solid portion 22 will maintain the implant 10 in the compressed or expanded position to provide the implant 10 with a desired medial-lateral width to fit the osteotomy site 12. As the first part 24 and the second part 26 are moved, the solid portion 22 bends at the hinge 42. The implant 10 is retained within the osteotomy site 12 due to friction between the portion of the tibia 14 at the osteotomy site 12 and the porous portion 20. The implant 10 will be further retained within the osteotomy site 12 by bone ingrowth into the porous portion 20. The implant 10 can also be retained within the osteotomy site 12 with any suitable retention device or feature, such as a suitable locking plate.

Figure 3:
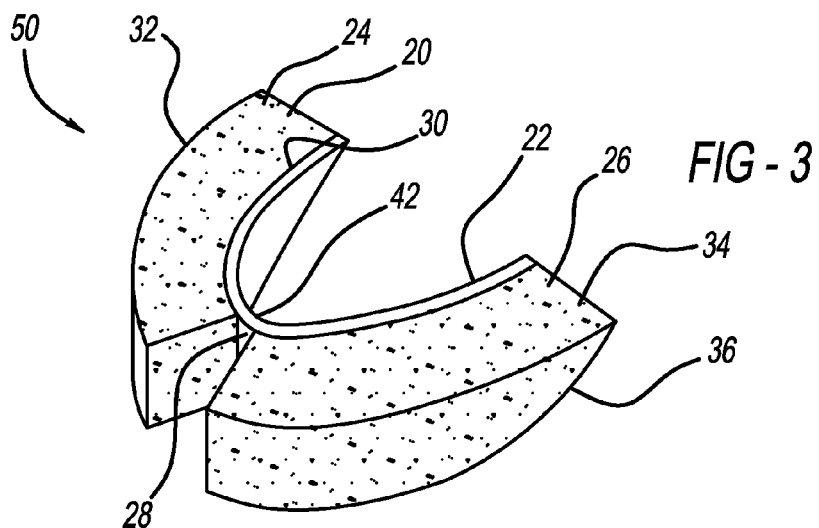
FIG. 3 is a perspective view of another osteotomy implant according to the present teachings.

With additional reference to FIG. 3, another osteotomy implant according to the present teachings is illustrated at reference numeral 50. The implant 50 is similar to the implant 10, and thus similar features are designated with similar reference numbers, and the description of these similar features set forth above in the description of the implant 10 also applies to the implant 50. The implant 50 can also be formed of the same material as the implant 10, and manufactured in the same manner. Unlike the implant 10, the solid portion 22 of the implant 50 is at the inner surface 30 of the porous portion 20. Providing the solid portion 22 at the inner surface 30 will typically increase the overall structural integrity of the implant 50.

Figure 4:
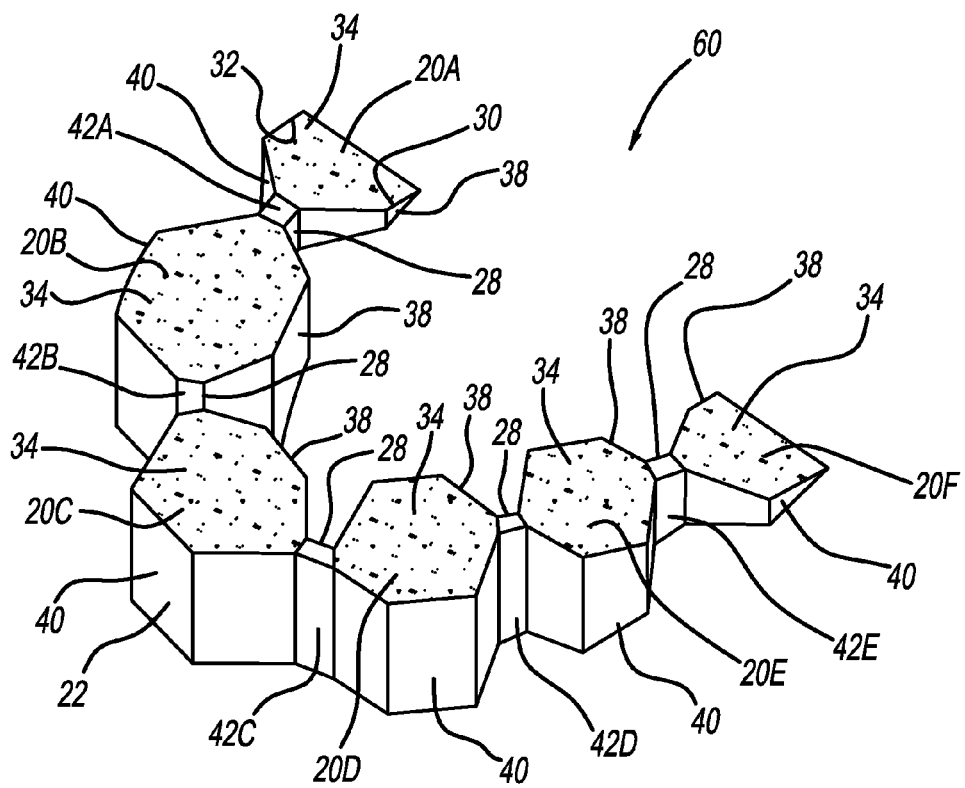
FIG. 4 is a perspective view of an additional osteotomy implant in accordance with the present teachings.

Another osteotomy implant according to the present teachings is illustrated in FIG. 4 at reference numeral 60. The implant 60 is similar to the implant 10, and thus similar features are designated with similar reference numbers, and the description of these similar features set forth above in the description of the implant 10 also applies to the implant 60. The implant 60 can also be formed of the same material as the implant 10, and manufactured in the same manner.

The porous portion 20 of the implant 60 is divided into a plurality of porous parts 20A through 20F. Each of the porous parts 20A-20F is surrounded by the solid portion 22. Between adjacent ones of the porous parts 20A-20F, the solid portion 22 includes the hinge 42, and thus a plurality of hinges 42A-42E are provided to link together the plurality of porous parts 20A-20F. Any suitable number of porous portions 20 can be included with the implant 60 depending on the size of the osteotomy site 12. To optimize fit between the implant 60 and the osteotomy site 12, the implant 60 can be flexed or compressed either inward or outward at any of the hinges 42A-42E, allowing the implant 60 to be flexed or compressed to nearly an infinite number of positions. The porous portions 20 define therebetween a plurality of clearances or gaps 28 that allow the implant 60 to be flexed inward and outward at the hinges 42. The width of the clearances or gaps 28 can be set to limit the amount of flex between the porous portions 20. The porous portions 20A-20F are exposed at the upper surfaces 34 and the under surfaces 36 thereof in order to permit bone growth therein, which further secures the implant 60 at the osteotomy site 12. The thickness of the hinge 42 can be adjusted to control the flexibility of the hinge 42.

Another osteotomy implant according to the present teachings is illustrated in FIG. 5 at reference numeral 70. The implant 70 is similar to the implant 10, for example, and thus like features are illustrated and described using similar reference numbers. The implant 70 can also be manufactured in the same way described above with respect to the implant 10. Unlike the implant 10, the implant 70 includes a hinge 42 with a ball 42F and a socket 42G. The ball 42A extends from the first solid portion 22A of the first part 24 of the porous portion 20. The socket 42G is defined within second solid portion 22B of the second part 26 of the porous portion 20. The clearance or gap 28 is defined between the first part 24 and the second part 26 of the porous portion 20. The ball and socket hinge 42F/42G can be formed in any suitable manner, such as using electron beam melting or direct metal laser sintering, which allows the ball and socket hinge 42F/42G to be "printed" together with the rest of the implant 70, such as by direct metal laser sintering or any other additive metal fabrication technique. Other suitable hinges include, for example, a barrel hinge and a butt hinge.

The ball and socket hinge 42F/42G facilitates movement of the first part 24 and the second part 26 of the porous portion 20 together or apart in order to decrease or increase the medial-lateral width of the implant to correspond to the implant site 12. When set at the desired medial-lateral width, the ball and socket hinge 42F/42G will retain the implant 70 at the set width in any suitable manner, such as by friction between the ball 42F and the socket 42G, or with any suitable locking device. Although the implant 70 is not illustrated with the first solid portion 22A extending entirely across the outer surface 32 of each of the first part 24 of the porous portion 20, the first solid portion 22A can be lengthened to extend entirely across the outer surface 32 of the first part 24. Similarly, the second solid portion 22B can be lengthened so as to extend across the entire outer surface 32 of the second part 26 of the porous portion 20. The ball 42F and the socket 42G can be provided in place of the hinge 42 of any one of the implants 10, 50, or 60, as well as the implants 80 and 90 described herein.

Yet another osteotomy implant according to the present teachings is illustrated in FIG. 6 at reference numeral 80. The implant 80 is similar to the implant 10 of FIG. 2, and thus like reference numerals are used to illustrate the similar features. The description of these like features set forth in the description of the implant 10 also applies to the implant 80. The implant 80 can be manufactured in the same manner set forth above with respect to the implant 10. Unlike the implant 10, the implant 80 includes an adjustment member, such as a fastener 82, extending through an aperture 84 defined in the solid portion 22. The fastener 82 also extends through portions of the porous portion 20 from the second part 26 to the first part 24, and thus spans the clearance or gap 28 therebetween. The fastener 82 can be threaded directly into the first part 24, or the first part 24 can include a threaded receptacle 86 to cooperate with the fastener 82. The fastener 82 facilitates compression and expansion of the first part 24 and the second part 26 of the porous portion 20. Specifically, as the fastener 82 is rotated in a first direction, such as with a suitable device, the fastener 82 will draw the first and second parts 24 and 26 together. As the fastener 82 is rotated in a second direction, the fastener 82 will push the first and second parts 24 and 26 apart. This will cause the solid portion 22 to generally bend about the hinge 42. The fastener 82 can be provided with any one of the implants 10, 50, 60, or 70.

FIG. 7 illustrates another osteotomy implant according to the present teachings at reference numeral 90. The implant 90 is similar to the implant 10, and thus features in common with the implant 10 are illustrated using common reference numbers. The solid portion 22 defines an aperture 92 proximate to hinge 42 of the implant 90. Seated within and extending through the aperture 92 is an adjustment member, such as a fastener 94. The fastener 94 is threaded into a nut 96 seated between the first part 24 and the second part 26 of the porous portion 20. Specifically, the nut 96 abuts the inner surface 30 of each of the first and second parts 24 and 26. As the screw is rotated with a suitable device, the screw will further cooperate with threads of the nut 96 to draw the nut 96 toward the solid portion 22, thereby causing the nut 96 to apply pressure to each of the inner surfaces 30 of the first and second parts 24 and 26 to force the first part 24 and the second part 26 apart, and thus increase the width of the implant 90 to fit a wider osteotomy site 12 from a first dimension to a second greater dimension.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of implanting an osteotomy implant at an osteotomy site, the method comprising:
   forming a cut in bone to create an osteotomy site with a first bone surface on a first side of the cut and a second bone surface on a second side of the cut;
   providing or obtaining a pre-assembled osteotomy implant comprising a first part, a second part, and a hinge to facilitate compression or expansion of the osteotomy implant, wherein the first and second parts of the osteotomy implant are non-removably joined via the hinge;
   comparing a width of the pre-assembled osteotomy implant to a width of the osteotomy site;
   if the width of the pre-assembled osteotomy implant is wider than the width of the osteotomy site, compressing the implant along the hinge to decrease the width of the osteotomy implant;
   if the width of the pre-assembled osteotomy implant is narrower than the width of the osteotomy site, expanding the implant along the hinge to increase the width of the osteotomy implant; and
   implanting the pre-assembled osteotomy implant into the osteotomy site so that the pre-assembled osteotomy implant engages the first and second bone surfaces of the osteotomy site; and moving an adjustable member that engages the first and second parts of the osteotomy implant to move the first and second parts relative to each other and thereby increase or decrease the width of the osteotomy implant.

2. The method of claim 1, further comprising bending the hinge to either compress or expand the width of the osteotomy implant.

3. The method of claim 1, wherein the osteotomy implant includes a first porous part and a second porous part coupled to a flexible solid portion defining the hinge, wherein compressing or expanding the osteotomy implant further comprises moving the first part relative to the second part at the hinge.

4. The method of claim 1, wherein providing or obtaining a pre-assembled osteotomy implant comprises:
   selecting the pre-assembled osteotomy implant from a plurality of pre-assembled osteotomy implants based upon the width of the osteotomy site.

5. The method of claim 1, wherein the osteotomy implant comprises a porous portion abutting a solid portion, and the method further comprises positioning the solid portion in the osteotomy site so that the solid portion defines an outwardly-facing wall facing outside of the osteotomy site, the wall preventing tissue growth into the porous portion.

6. The method of claim 5, further comprising contacting a first surface of the porous portion with the first bone surface of the osteotomy site and contacting a second surface of the porous portion with the second bone surface of the osteotomy site.

7. The method of claim 1, further comprising fixing the first and second parts of the osteotomy implant relative to each other using the adjustment member.

8. A method of implanting an osteotomy implant at an osteotomy site, the method comprising:
   forming a cut in bone to create an osteotomy site with a first bone surface on a first side of the cut and a second bone surface on a second side of the cut;
   providing an osteotomy implant comprising:
      a porous portion configured for bone growth and including a first part with a first sidewall and a second part with a second sidewall, a clearance provided between the first and second sidewalls;
      a solid portion configured to inhibit tissue growth into the porous portion from outside of the osteotomy site, the solid portion abutting the porous portion, the first and second sidewalls of the porous portion extending from the solid portion to define the clearance; and
      a hinge portion configured to enable the implant to be adjustable by either compressing the implant relative to the hinge to decrease the clearance or expanding the implant relative to the hinge to increase the clearance;
   determining a size of the osteotomy site;
   comparing a size of the osteotomy implant to the size of the osteotomy site;
   adjusting the osteotomy implant between a first configuration and a second configuration to accommodate the osteotomy site; and
   implanting the osteotomy implant into the osteotomy site so that the osteotomy implant engages the first and second bone surfaces of the osteotomy site; fixing the first and second parts of the porous portion relative to each other using an adjustment member; and moving the adjustment member to increase or decrease the clearance between the first and second sidewalls.

9. The method of claim 8, wherein the solid portion is bendable at the hinge portion to compress or expand the first and second parts relative to each other to increase or decrease a distance of the clearance.

10. The method of claim 8, wherein the hinge portion is selected from a group consisting of a flexible solid portion positioned relative to the clearance between the first part and the second part, a ball and socket hinge, and a flexible solid hinge having an adjustment member to be actuated to move the first part relative to the second part.

11. The method of claim 8, wherein the first and second parts of the porous portion are non-removably joined via the hinge portion.

12. The method of claim 8, further comprising positioning the solid portion in the osteotomy site so that the solid portion defines an outwardly-facing wall facing towards the outside of the osteotomy site.

13. The method of claim 8, wherein the porous portion includes non-porous ribs extending inside the porous portion.

14. The method of claim 8, further comprising contacting a first surface of the porous portion with the first bone surface of the osteotomy site and contacting a second surface of the porous portion with the second bone surface of the osteotomy site.

* * * * *